United States Patent [19]
Horstmann et al.

[11] Patent Number: 5,206,225
[45] Date of Patent: Apr. 27, 1993

[54] ALKYLCARBOXYLIC ACID DIMETHYLAMIDES AS CRYSTALLIZATION INHIBITORS

[75] Inventors: Heinz-Otto Horstmann, Bergisch-Gladbach; Uwe Priesnitz, Solingen; Ulrich Engelhardt, Leverkusen; Karl Reizlein, Cologne; Klaus Wangermann, Krefeld, all of Fed. Rep. of Germany

[73] Assignee: Bayer Aktiengesellschaft, Leverkusen, Fed. Rep. of Germany

[21] Appl. No.: 688,183

[22] Filed: Apr. 19, 1991

[30] Foreign Application Priority Data

Apr. 27, 1990 [DE] Fed. Rep. of Germany ....... 4013522

[51] Int. Cl.$^5$ .................. A01N 43/04; A01N 55/00; C07D 249/00; C07D 249/08
[52] U.S. Cl. .................................. 514/63; 514/383; 514/625; 548/110; 548/268.2; 548/267.4; 548/267.8
[58] Field of Search .................. 514/63, 383, 625; 548/110, 267.4, 268.2, 267.8

[56] References Cited

U.S. PATENT DOCUMENTS 3,342,673  9/1967  Kaufman et al. ............... 514/481

FOREIGN PATENT DOCUMENTS 0077078  4/1983  European Pat. Off. .
0391168  10/1990  European Pat. Off. .
0391171  10/1990  European Pat. Off. .
0095242  11/1983  PCT Int'l Appl. .
8701391  1/1988  World Int. Prop. O. .

Primary Examiner—Allen J. Robinson
Attorney, Agent, or Firm—Sprung Horn Kramer & Woods

[57] ABSTRACT

Crystallization of active material in spraying an aqueous solution of one of

[structure II with $R^1$, $R^2$, $R^3$ and triazole]

[structure III with $R^4$-phenyl-O-CH-Y-C(CH$_3$)$_3$ and triazole]

[structure IV with Cl-phenyl($R^5$)-CH=C-CH(OH)-C(CH$_3$)$_3$ and triazole]

and is prevented by incorporation therein of an alkylcarboxylic acid dimethylamide of the formula $$R-CO-N(CH_3)_2 \quad (I)$$

in which R represents alkyl having 5 to 19 carbon atoms.

10 Claims, 3 Drawing Sheets

ALKYLCARBOXYLIC ACID DIMETHYLAMIDES AS CRYSTALLIZATION INHIBITORS

The present invention relates to the new use of certain alkylcarboxylic acid dimethylamides for prevention of crystallization during the application of aqueous spray liquors based on specific pesticidally active compounds.

In spray equipment which is customarily used for the application of aqueous formulations of plant treatment agents, several filters and nozzles are present. Thus, for example, suction filters are situated between suction component and tank pump and in addition pressure filters are located in the pressure region downstream of the pump. In addition, nozzle filters may also be present which are situated directly upstream of the spray nozzles. All these filters and also the nozzles can block more or less easily as a result of crystallizing active compound during the application of aqueous spray liquors based on solid active compounds.

It is already known that the azole derivatives mentioned below are fungicidally active and can be applied in the form of aqueous spray liquors to plants and/or their environment:

1-(4-chlorophenyl)-4,4-dimethyl-3-(1,2,4-triazol-1-yl-methyl)-pentan-3-ol, 1-(4-chlorophenoxy)-3,3-dimethyl-1-(1,2,4-triazol-1-yl)-butan-2-one, 1-(4-chlorophenoxy)-3,3-dimethyl-1-(1,2,4-triazol-1-yl)-butan-2-ol, 1-(4-phenyl-phenoxy)-3,3-dimethyl-1-(1,2,4-triazol-1-yl)-butan-2-ol, 1-(2-chlorophenyl)-2-(1-chloro-cycloprop-1-yl)-3-(1,2,4-triazol-1-yl)-propan-2-ol, 1-(4-fluorophenyl)-1-(2-fluorophenyl)-2-(1,2,4-triazol-1-yl)ethan-1-ol, 1-(1,2,4-triazol-1-yl)-2-(2,4-dichlorophenyl)-hexan-2-ol, 1-[bis-(4-fluorophenyl)-methyl-silyl]-1H-(1,2,4-triazole), 1-(4-chlorophenyl)-2-(1,2,4-triazol-1-yl)-4,4-dimethyl-pent-1-en-3-ol, 1-(2,4-dichlorophenyl)-2-(1,2,4-triazol-1-yl)-4,4-dimethyl-pent-1-en-3-ol, 1-(4-chlorophenyl)-1-(1-cyclopropyl-ethyl)-2-(1,2,4-triazol-1-yl)-ethan-1-ol and 1-(4-chlorophenyl)-3-phenyl-3-cyano-4-(1,2,4-triazol-1-yl)-butane (compare EP-OS (European Published Specification) 0,040,345, DE-PS (German Patent Specification) 2,201,063, DE-PS (German Patent Specification) 2,324,010, EP-OS (European Published Specification) 0,297,345, EP-OS (European Published Specification) 0,015,756, U.S. Pat. No. (U.S. Pat. No.) 4,551,469, EP-OS (European Published Specification) 0,068,813, DE-OS (German Published Specification) 2,838,847, DE-OS (German Published Specification) 3,010,560, DE-OS (German Published Specification) 3,406,993 and DE-OS (German Published Specification) 2,821,971).

Surface-active substances, such as, for example, alkylaryl polyglycol ethers can be employed for the preparation of spray liquors of this type. However, a disadvantage in the use of these conventional formulations is that the active compounds often tend to crystallize and both filters and nozzles of the spray equipment can block.

It has now been found that alkylcarboxylic acid dimethylamides of the formula $$R-CO-N\begin{matrix}CH_3\\CH_3\end{matrix} \quad (I)$$

in which R represents alkyl having 5 to 19 carbon atoms, can be used during application of aqueous spray liquors which contain A) at least one azole derivative of the formula $$R^1-\underset{\underset{\underset{N}{|}}{\underset{CH_2}{|}}}{\overset{\overset{R^3}{|}}{C}}-R^2 \quad (II)$$

(with triazole ring)

in which a) $R^1$ represents

—CH$_2$—CH$_2$—C$_6$H$_4$—Cl $R^2$ represents tert.-butyl and
$R^3$ represents hydroxyl, or b) $R^1$ represents 4-fluorophenyl,
$R^2$ represents 2-fluorophenyl and
$R^3$ represents hydroxyl, or c) $R^1$ represents 2,4-dichlorophenyl,
$R^2$ represents n-butyl and
$R^3$ represents hydroxyl, or d) $R^1$ represents —CH$_2$—CH$_2$—C$_6$H$_4$—Cl $R^2$ represents phenyl and
$R^3$ represents cyano, or e) $R^1$ represents 2-chloro-benzyl,
$R^2$ represents 1-chloro-cycloprop-1-yl and
$R^3$ represents hydroxyl, or f) $R^1$ represents 4-chlorophenyl,
$R^2$ represents

—CH(CH$_3$)-cyclopropyl and
$R^3$ represents hydroxyl, and/or at least one azole derivative of the formula in which
a) Y represents —CH(OH) and
R⁴ represents chlorine or phenyl, or
b) Y represents CO and
R⁴ represents chlorine, and/or
at least one azole derivative of the formula (IV)

in which R⁵ represents hydrogen or chlorine, and/or
1-[bis-(4-fluorophenyl)-methyl-silyl]-1H-(1,2,4-triazole) of the formula (V)

and

B) if desired, one or more other active compounds and additives
for prevention of crystallization of active compounds of the formulae (II) to (V).

It is extremely surprising that the crystallization tendency of azole derivatives of the formulae (II) to (V) is greatly reduced by the use according to the invention of alkylcarboxylic acid dimethylamides of the formula (I). Above all, it was not to be expected that alkylcarboxylic acid dimethylamides of the formula (I) would be substantially better suited than other comparably acting substances for the purpose indicated.

The use of alkylcarboxylic acid dimethylamides of the formula (I) in aqueous or non-aqueous formulations based on fungicidally active azole derivatives of the formulae (II) to (V) has a number of advantages. Thus, the alkylcarboxylic acid dimethylamides are substances which can be handled without problems and are also available in relatively large amounts. In addition, during spraying of aqueous formulations which contain active compounds of the formulae (II) to (V), the use of the substances of the formula (I) prevents both the filters and the nozzles of the spray equipment from blocking. It is also advantageous that alkylcarboxylic acid dimethylamides of the formula (I) have no undesired side effects in plant protection.

Formula (I) defines the alkylcarboxylic acid dimethylamides which can be used according to the invention. R represents straight-chain or branched alkyl with 5 to 19 carbon atoms, preferably with 5 to 11 carbon atoms. The substances can be used both individually and in the form of mixtures. A mixture which can particularly preferably be used is that known under the commercial name Hallcomid, which consists on average of 5% of hexanecarboxylic acid dimethylamide, 50% of octanecarboxylic acid dimethylamide, 40% of decanecarboxylic acid dimethylamide and 5% of dodecanecarboxylic acid dimethylamide.

The alkylcarboxylic acid dimethylamides of the formula (I) are already known.

The formulae (II) to (V) define the azole derivatives contained in the aqueous spray liquors which can be used according to the invention. Individual or, alternatively, several of the following azole derivatives can be present.

1-(4-chlorophenyl)-4,4-dimethyl-3-(1,2,4-triazol-1-yl-methyl)-pentan-3-ol of the formula (II-a)

1-(4-fluorophenyl)-1-(2-fluorophenyl)-2-(1,2,4-triazol-1-yl)-ethan-1-ol of the formula (II-b)

1-(1,2,4-triazol-1-yl)-2-(2,4-dichlorophenyl)-hexan-2-ol of the formula (II-c)

1-(4-chlorophenyl)-3-phenyl-3-cyano-4-(1,2,4-triazole-1-yl)-butane of the formula (II-d)

1-(2-chlorophenyl)-2-(1-chloro-cycloprop-1-yl)-3-(1,2,4-triazol-1-yl)-propan-2-ol of the formula (II-e)

1-(4-chlorophenyl)-1-(1-cyclopropyl-ethyl)-2-(1,2,4-triazol-1-yl)-ethan-1-ol of the formula (II-f)

1-(4-chlorophenoxy)-3,3-dimethyl-1-(1,2,4-triazol-1-yl)-butan-2-ol of the formula (III-a)

1-(4-phenyl-phenoxy)-3,3-dimethyl-1-(1,2,4-triazol-1-yl)-butan-2-ol of the formula (III-b)

1-(4-chlorophenoxy)-3,3-dimethyl-1-(1,2,4-triazol-1-yl)-butan-2-one of the formula (III-c)

1-(4-chlorophenyl)-1-(1,2,4-triazol-1-yl)-4,4-dimethyl-pent-1-en-3-ol of the formula (IV-a)

1-(2,4-dichlorophenyl)-2-(1,2,4-triazole-1-yl)-4,4-dimethyl-pent-1-en-3-ol of the formula (IV-b)

1-[bis-(4-fluorophenyl)-methyl-silyl]-1H-(1,2,4-triazole) of the formula (V)

The active compounds of the formulae (II) to (V) and their use for combating phytopathogenic fungi are known (compare EP-OS (European Published Specification) 0,040,345, U.S. Pat. No. 4,551,469, EP-PS (European Patent Specification) 0,015,756, EP-OS (European Published Specification) 0,068,813, EP-OS (European Published Specification) 0,297,345, DE-OS (German Published Specification) 3,406,993, DE-PS (German Patent Specification) 2,324,010, DE-PS (German Patent Specification) 2,838,847, DE-OS (German Published Specification) 3,010,560 and DE-OS (German Published Specification) 2,821,971).

The active compounds of the formulae (II) to (V) can be employed in customary formulations. Preferably, they are applied in the form of aqueous spray liquors.

In addition to the active compounds of the formulae (II) to (V), one or more other active compounds can also be present in the spray liquors which can be used according to the invention. Those which are preferably suitable in this case are compounds having fungicidal properties. Examples of active compounds of this type which can additionally be used and which may be mentioned are:

N,N-dimethyl-N'-phenyl-(N'-fluorodichloromethylthio)-sulphamide (dichlofluanid),
N,N-dimethyl-(N'-fluorodichloromethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol),
N-trichloromethylthio-phthalimide (folpet),
N-dodecyl-guanidine acetate (dodine),
tetrachloro-isophthalo-dinitrile (chlorothalonil),
4,5,6,7-tetrachlorophthalide, zinc-ethylene-bis-dithiocarbamate (zineb),
manganese-ethylene-bis-dithiocarbamate (maneb),
zinc-ethylene-bis-dithiocarbamate/manganese-ethylene-bis-dithiocarbamate (mancozeb),
zinc-propylene-1,2-bis-dithiocarbamate (propineb),
1-[3-(4-(1,1-dimethylethyl)-phenyl)-2-methylpropyl]-piperidine (fenpropidin),
N-tridecyl-2,6-dimethyl-morpholine (tridemorph),
N-dodecyl-2,6-dimethyl-morpholine (aldimorph)
2-[2-(2,4-dichlorophenyl)-2-(2-propenyloxy)-ethyl]-imidazole (imazalil),
N-[2-(2,4,6-trichlorophenoxy)-ethyl]-N-propyl-1H-imidazole (prochloraz),
1,2-dimethyl-cyclopropane-1,2-dicarboxylic acid-3,5-dichlorophenylimide (procymidone),
2-methoxycarbamoyl-benzimidazole (carbendazim),
1-(butylcarbamoyl)-2-benzimidazolylmethyl carbamate (benomyl),
2,4-dichloro-6-(2'-chlorophenyl-amino)-1,3,4-triazine (anilazine),
bis-(8-guanidine-O-octyl)-amine triacetate (guazatine),
1-(4-chlorobenzyl)-1-cyclopentyl-3-phenyl-urea (pencycuron)

Suitable additives which can be present in the spray liquors which can be used according to the invention are surface-active substances, organic diluents, water, acids, low-temperature stabilizers and adhesives.

Possible surface-active substances in this case are non-ionic and anionic emulsifiers, such as polyoxyethylene fatty acid esters, polyoxyethylene fatty alcohol ethers, alkylaryl polyglycol ethers, alkylsulphonates, alkylarylsulphonates, alkyl sulphates and aryl sulphonates. The emulsifiers can be employed individually or, alternatively, in a mixture. Those which may preferably be mentioned are polyoxyethylene sorbitan monolaurate having on average 20 oxyethylene units per molecule,
polyoxyethylene sorbitan monopalmitate having on average 20 oxyethylene units per molecule,
polyoxyethylene sorbitan monostearate having on average 20 oxyethylene units per molecule,
sorbitan monolaurate,
sorbitan monopalmitate,
sorbitan monostearate,
polyoxyethylene oleyl ether having on average 10 oxyethylene units per molecule,
polyoxyethylene oleyl ether having on average 20 oxyethylene units per molecule,
bis-[α-methyl-(4-methyl-benzyl)]-phenyl polyglycol ether having on average 27 oxyethylene units per molecule,
bis-[α-methyl-(4-n-dodecyl)]-phenyl polyglycol ether having on average 27 oxyethylene units per molecule,
bis-(4-methyl-benzyl)-phenyl polyglycol ether having on average 27 oxyethylene units per molecule,
bis-(4-n-dodecyl-benzyl)-phenyl polyglycol ether having on average 27 oxyethylene units per molecule,
tris-[α-methyl-(4-methyl-benzyl)]-phenyl polyglycol ether having on average 17 oxyethylene units per molecule,
bis-(α-methyl-benzyl)-phenyl polyglycol ether having on average 17 oxyethylene units per molecule,
tris-(α-methyl-benzyl)-phenyl polyglycol ether having on average 17 oxyethylene units per molecule,
bis-(α-methyl-benzyl)-phenyl polyglycol ether having on average 27 oxyethylene units per molecule,
tris-(α-methyl-benzyl)-phenyl polyglycol ether having on average 27 oxyethylene units per molecule,
bis-(α-methyl-benzyl)-phenyl polyglycol ether having on average 3 oxyethylene units per molecule,
tris-(α-methyl-benzyl)-phenyl polyglycol ether having on average 3 oxyethylene units per molecule,
nonylphenol polyglycol ether having on average 15 oxyethylene units per molecule,
nonylphenol diglycol ether having on average 2 oxyethylene units per molecule,
n-dodecyl sodium sulphonate,
sodium lauryl sulphate,
4-(n-nonyl)-phenyl-sulphonic acid sodium salt,
4-(tetrapropylene)-phenyl-sulphonic acid sodium salt,
4-(i-dodecyl)-phenyl-sulphonic acid ammonium salt,
4-(i-dodecyl)-phenyl-sulphonic acid calcium salt,
4-(n-dodecyl)-phenyl-sulphonic acid (2-hydroxyethyl)-ammonium salt,
4-(n-dodecyl)-phenyl-sulphonic acid bis-(2-hydroxyethyl)-ammonium salt,
4-(n-dodecyl)-phenyl-sulphonic acid tris-(2-hydroxyethyl) ammonium salt,
4-(n-dodecyl)-phenyl-sulphonic acid calcium salt, The emulsifiers from the alkylaryl polyglycol ether group used in practice are in general mixtures of several compounds. In particular, in this case they are mixtures of substances which differ by the degree of substitution on the phenyl ring connected to the oxyethylene unit and the number of oxyethylene units. As a result, fractional numbers are also calculated as average values for the number of substituents on the phenyl ring. For example, substances may be mentioned for which the following average compositions result:

Organic diluents which can be present in the spray liquors which can be used according to the invention are all polar and non-polar organic solvents which can customarily by employed for purposes of this type. Those which are preferred are ketones, such as methyl isobutyl ketone and cyclohexanone, in addition amides, such as dimethylformamide and furthermore cyclic compounds, such as N-methyl-pyrrolidone, N-octyl-pyrrolidone, N-dodecyl-pyrrolidone, N-dodecyl-caprolactam and butyrolactone, and moreover strongly polar solvents, such as dimethyl sulphoxide, and in addition aromatic hydrocarbons, such as xylene, moreover esters, such as propylene glycol monomethyl ether acetate, dibutyl adipate, hexyl acetate, heptyl acetate, tri-n-butyl citrates and di-n-butyl phthalate, and furthermore alcohols, such as ethanol, n- and i-propanol, n- and i-butanol, n- and i-amyl alcohol, benzyl alcohol and 1-methoxypropan-2-ol.

Prior to diluting the formulations, water can also be present in the spray liquors which can be used according to the invention.

Acids which can be present in the spray liquors which can be used according to the invention are all inorganic and organic acids which can customarily be employed for purposes of this type. Those which are preferred are aliphatic and aromatic hydroxycarboxylic acids, such as citric acid, salicylic acid, tartaric acid and ascorbic acid, and also inorganic acids, such as phosphoric acid.

Low-temperature stabilizers which can be present in the spray liquors which can be used according to the invention are all substances customarily suitable for this purpose. Those which are preferred are urea, glycerol and propylene glycol.

Adhesives which can be employed in the spray liquors which can be used according to the invention are all substances which are customarily suitable for this purpose. Those which are preferred are adhesives such as carboxymethyl cellulose, natural and synthetic pulverulent, granular or latex-like polymers, such as gum arabic, polyvinyl alcohol, polyvinyl acetate, and natural phospholipids, such as cephalins and lecithins, and also synthetic phospholipids. Other additives can be mineral and vegetable oils.

Otherwise, water is in each case present in the spray liquors which can be used according to the invention.

The active compound concentrations can be varied within a specific range in the spray liquors which can be used according to the invention. In general, the active compound concentrations are between 0.0001 and 3 percent by weight, preferably between 0.001 and 2 percent by weight.

The ratio of active compound of the formulae (II) to (V) to alkylcarboxylic acid dimethylamide of the formula (I) can also be varied within a specific range. In general, the weight ratio of active compound from the group (A) to alkylcarboxylic acid dimethylamide of the formula (I) is between 1:0.2 and 1:5, preferably between 1:0.6 and 1:2.

The amounts of other active compounds or additives can be varied within a relatively wide range in the spray liquors which can be used according to the invention. They are of the order of magnitude which is customarily the case in aqueous spray liquors of this type.

The spray liquors which can be used according to the invention are prepared by customary methods. In general, a procedure is used in which a concentrate is first prepared by adding together the required components in any desired sequence at temperatures between 10° and 30° C. and homogeneously mixing and if desired filtering the resulting mixture. To prepare the ready-to-use spray liquors, the concentrated formulation is mixed, if desired with stirring and/or pumping, with the amount of water desired in each case such that the formulation is distributed in water uniformly and in finely disperse form.

It is also possible to add alkylcarboxylic acid dimethylamide of the formula (I) when the concentrate is diluted with water to give the ready-to-use spray liquor.

Both for the preparation of the concentrated formulations and for the preparation and application of the spray liquors which can be used according to the invention, all mixers and spray equipment which are customarily suitable for this purpose can be employed.

As a result of the use of alkylcarboxylic acid dimethylamides of the formula (I) in aqueous spray liquors based on active compounds of the formulae (II) to (V), the crystallization of active compound both in the concentrated commercial formulation and during application of the aqueous spray liquors prepared from this is either completely suppressed or on the whole prevented in the filters and outlet openings of the spray equipment such that the application of the spray liquors is not impaired.

The preparation and the crystallization behavior of the spray liquors which can be used according to the invention are illustrated by the following examples, taken in conjunction with the accompanying drawings wherein.

PREPARATION EXAMPLES

Example 1

For the preparation of a formulation 25.4 parts by weight of 1-(4-chlorophenyl)-4,4-dimethyl-3-(1,2,4-triazol-1-yl-methyl)-pentan-3-ol of the formula 49.1 parts by weight of a mixture of on average

5% hexanecarboxylic acid dimethylamide,

50% octanecarboxylic acid dimethylamide,

40% decanecarboxylic acid dimethylamide and

5% dodecanecarboxylic acid dimethylamide,

20.0 parts by weight of the emulsifier of the average composition of the formula

5.0 parts by weight of N-methyl-pyrrolidone and 0.5 parts by weight of water, are mixed at room temperature and stirred to give a homogeneous liquid. By mixing with water, a spray liquor is prepared from the concentrate thus obtained in which the concentrate is present in a concentration of 0.5% by weight.

Example 2

For the preparation of a formulation 25.0 parts by weight of 1-(4-chlorophenyl)-4,4-dimethyl-3-(1,2,4-triazol-1-yl-methyl)-pentan-3-ol of the formula (IIa)

35.0 parts by weight of a mixture of on average
5% hexanecarboxylic acid dimethylamide,
50% octanecarboxylic acid dimethylamide,
40% decanecarboxylic acid dimethylamide and
5% dodecanecarboxylic acid dimethylamide,
6.5 parts by weight of the emulsifier of the average composition of the formula

10.0 parts by weight of N-octyl -pyrrolidone, 6.5 parts by weight of 4-(n-dodecyl)-phenyl-sulphonic acid (2-hydroxyethyl)-ammonium salt and 17.0 parts by weight of water, are mixed at room temperature and stirred to give a homogeneous liquid. By mixing with water, a spray liquor is prepared from the concentrate thus obtained in which the concentrate is present in a concentration of 0.5% by weight.

Example 3

For the preparation of a formulation 24.2 parts by weight of 1-(4-chlorophenyl)-4,4-dimethyl-3-(1,2,4-triazol-1-yl-methyl)-pentan-3-ol of the formula (IIa)

12.1 parts by weight of 1-(4-chlorophenoxy)-3,3-dimethyl-1-(1,2,4-triazol-1-yl)-butan-2-ol of the formula (IIIa)

35.0 parts by weight of a mixture of on average,
5% hexanecarboxylic acid dimethylamide,
50% octanecarboxylic acid dimethylamide,
40% decanecarboxylic acid dimethylamide and
5% dodecanecarboxylic acid dimethylamide,
20.0 parts by weight of the emulsifier of the average composition of the formula and 8.7 parts by weight of N-methyl-pyrrolidone, are mixed at room temperature and stirred to give a homogeneous liquid. By mixing with water, a spray liquor is prepared from the concentrate thus obtained in which the concentrate is present in a concentration of 0.5% by weight.

Example 4

For the preparation of a formulation 23.8 parts by weight of 1-(4-chlorophenyl)-4,4-dimethyl-3-(1,2,4-triazol-1-yl-methyl)-pentan-3-ol of the formula (IIa)

11.9 parts by weight of 1-(4-chlorophenoxy)-3,3-dimethyl-1-(1,2,4-triazol-1-yl)-butan-2-ol of the formula (IIIa)

15.0 parts by weight of a mixture of on average
5% hexanecarboxylic acid dimethylamide,
50% octanecarboxylic acid dimethylamide,
40% decanecarboxylic acid dimethylamide and
5% dodecanecarboxylic acid dimethylamide,
12.0 parts by weight of N-octyl-pyrrolidone, 4.0 parts by weight of the emulsifier of the average composition of the formula

4.0 parts by weight of 4-(n-dodecyl)-phenyl-sulphonic acid (2-hydroxyethyl)-ammonium salt, 4.0 parts by weight of emulsifier of the average composition of the formula

8.0 parts by weight of an emulsifier which is obtained by reacting 1 mol of a branched dodecanol with 15 mols of ethylene oxide, and 17.3 parts by weight of N-methyl-pyrrolidone, are mixed at room temperature and stirred to give a homogeneous liquid. By mixing with water, a spray liquor is prepared from the concentrate thus obtained in which the concentrate is present in a concentration of 0.5% by weight.

Example 5

For the preparation of a formulation 25.0 parts by weight of 1-(4-chlorophenyl)-4,4-dimethyl-3-(1,2,4-triazol-1-yl-methyl)-pentan-3-ol of the formula (IIa)

35.0 parts by weight of a mixture of on average
5% hexanecarboxylic acid dimethylamide,
50% octanecarboxylic acid dimethylamide,
40% decanecarboxylic acid dimethylamide and
5% dodecanecarboxylic acid dimethylamide,
6.5 parts by weight of the emulsifier of the average composition of the formula

10.0 parts by weight of N-octyl-pyrrolidone, 6.5 parts by weight of 4-(n-dodecyl)-phenyl-sulphonic acid (2-hydroxyethyl)-ammonium salt, 5.0 parts by weight of N-methyl-pyrrolidone and 12.0 parts by weight of water, are mixed at room temperature and stirred to give a homogeneous liquid. By mixing with water, a spray liquor is prepared from the concentrate thus obtained in which the concentrate is present in a concentration of 0.5% by weight.

Comparison Example A

For the preparation of a formulation 12.5 parts by weight of 1-(4-chlorophenyl)-4,4-dimethyl-1,2,4-triazol-1-yl-methyl)-pentan-3-ol of the formula (II-a)

6.5 parts of the emulsifier of the average composition of the formula 6.5 parts by weight of 4-(n-dodecyl)-phenylsulphonic acid (2-hydroxyethyl)-ammonium salt, 35.0 parts by weight of cyclohexanone and 39.5 parts by weight of water are mixed at room temperature and stirred to give a homogeneous liquid. By mixing with water, a spray liquor is prepared from the concentrate thus obtained in which the concentrate is present in a concentration of 0.5% by weight.

Use Example I

To test the crystallization properties, 250 ml of an aqueous spray liquor which has a concentrate content of 0.5% by weight are in each case recirculated through a fine mesh sieve for 15 minutes with the aid of a pump in a flow-through apparatus. After repeating this process eight times with 250 ml of freshly employed spray liquor each time, the crystal deposition on the sieve is photographed.

The corresponding photographs are illustrated in FIGS. 1 to 5 (FIGS. 1 to 5).

Figure 1:
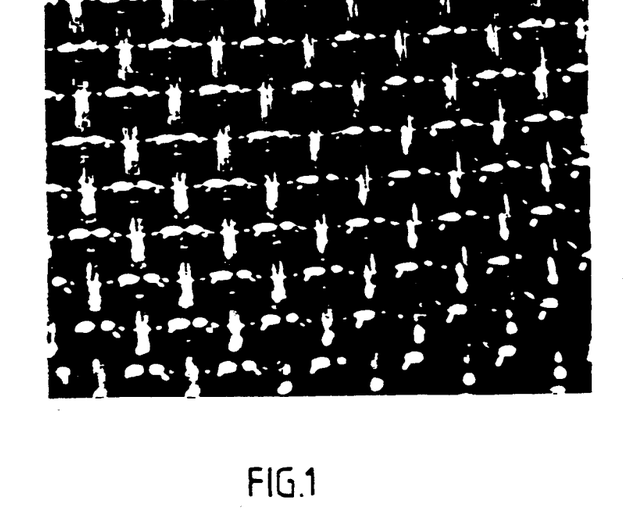
FIGS. 1 to 5 are photo enlargements of crystal deposits in accordance with the invention and the prior art.

FIG. 1 shows in an enlargement of 25 times the crystal deposition which results on the sieve on pumping through eight 250 ml batches of the spray liquor according to Example (1).

Figure 2:
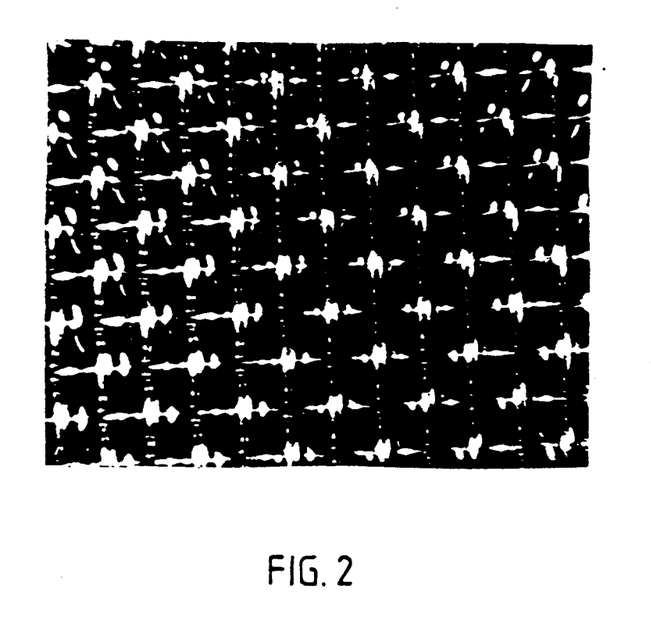

FIG. 2 shows in an enlargement of 25 times the crystal deposition which results on the sieve on pumping through eight 250 ml batches of the spray liquor according to Example (2).

Figure 3:
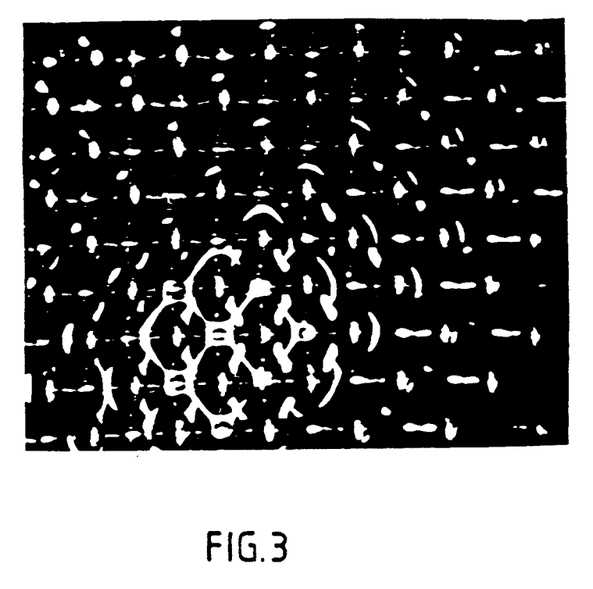

FIG. 3 shows in an enlargement of 25 times the crystal deposition which results on the sieve on pumping through eight 250 ml batches of the spray liquor according to Example (3).

Figure 4:
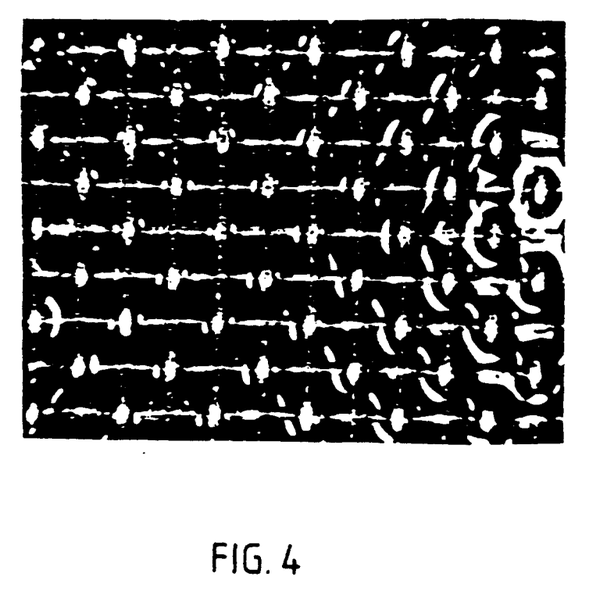

FIG. 4 shows in an enlargement of 25 times the crystal deposition which results on the sieve on pumping through eight 250 ml batches of the spray liquor according to Example (4).

Figure 5:
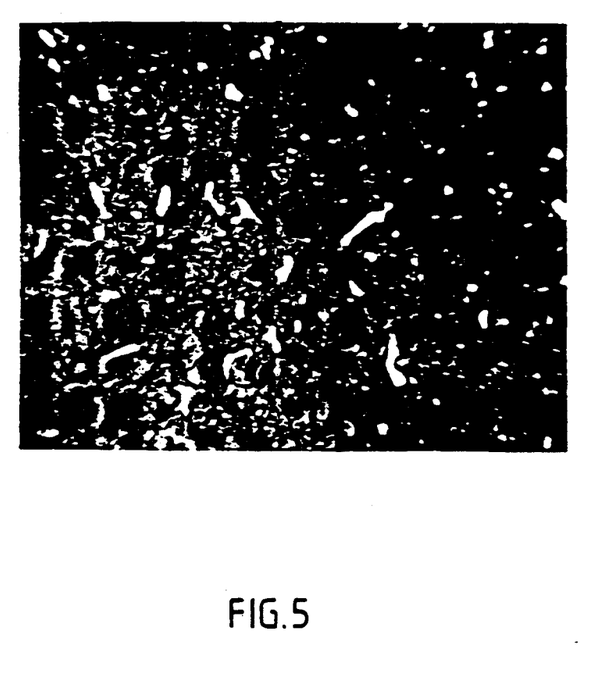

FIG. 5 shows in an enlargement of 25 times the crystal deposition which results on the sieve on pumping through eight 250 ml batches of the spray liquor according to Example (A).

From the figures, it is visible that the sieve in the case of the known spray liquor according to Example (A) is partially blocked, while in the case of the spray liquors according to Examples (1) to (4) no crystal deposition is observed.

It will be understood that the specification and examples are illustrative but not limitative of the present invention and that other embodiments within the spirit and scope of the invention will suggest themselves to those skilled in the art.

We claim:

1. A composition comprising an alkylcarboxylic acid dimethylamide of the formula (I)

in which

R represents alkyl having 5 to 11 carbon atoms, and
A) at least one compound selected from the group consisting of (II)

(III)

(IV)

and (V)

in which
a) R¹ represents

R² represents tert.-butyl and
R³ represents hydroxyl, or
b) R¹ represents 4-fluorophenyl,
R² represents 2-fluorophenyl and
R³ represents hydroxyl, or
c) R¹ represents 2,4-dichlorophenyl,
R² represents n-butyl and
R³ represents hydroxyl, or
d) R¹ represents R² represents phenyl and
R³ represents cyano, or
e) R¹ represents 2-chloro-benzyl,
R² represents 1-chloro-cycloprop-1-yl and
R³ represents hydroxyl, or
f) R¹ represents 4-chlorophenyl,

R² represents and

R³ represents hydroxyl, or
g) Y represents —CH(OH) and
R⁴ represents chlorine or phenyl, or
h) Y represents CO and
R⁴ represents chlorine, and
i) R⁵ represents hydrogen or chlorine, and optionally at least one member selected from the group consisting of a surface-active agent, organic diluent, water, low temperature stabilizer and adhesive, and wherein the weight ratio of active compound from the group (A) to alkylcarboxylic acid dimethylamide of the formula (I) is from about 1:0.2 to 1:5.

2. A composition according to claim 1, in which A is (II)

3. A composition according to claim 1, in which A is (III)

4. A composition according to claim 1, in which A is (IV)

5. A composition according to claim 1, in which A is (V)

6. A composition according to claim 1, in which (I) comprises an alkylcarboxylic acid dimethylamide mixture which on average comprises 5% of hexanecarboxylic acid dimethylamide,
50% of octanecarboxylic acid dimethylamide,
40% of decanecarboxylic acid dimethylamide and
5% of dodecanecarboxylic acid dimethylamide.

7. A composition according to claim 1, in which A is 1-(4-chlorophenyl)-4,4-dimethyl-3-(1,2,4-triazol-1-yl-methyl)-pentan-3-ol of the formula (IIa)

8. A composition according to claim 7, in which (I) comprises an alkylcarboxylic acid dimethylamide mixture which on average comprises

5% of hexanecarboxylic acid dimethylamide,
50% of octanecarboxylic acid dimethylamide,
40% of decanecarboxylic acid dimethylamide and
5% of dodecanecarboxylic acid dimethylamide.

9. A composition according to claim 1, dissolved in water.

10. In the spraying of an aqueous solution of an active compound selected from the group consisting of (II)

(III)

(IV)

and (V)

wherein
a) $R^1$ represents $R^2$ represents tert.-butyl and
$R^3$ represents hydroxyl, or
b) $R^1$ represents 4-fluorophenyl,
$R^2$ represents 2-fluorophenyl and
$R^3$ represents hydroxyl, or
c) $R^1$ represents 2,4-dichlorophenyl,
$R^2$ represents n-butyl and
$R^3$ represents hydroxyl, or
d) $R^1$ represents $R^2$ represents phenyl and
$R^3$ represents cyano, or
e) $R^1$ represents 2-chloro-benzyl,
$R^2$ represents 1-chloro-cycloprop-1-yl and
$R^3$ represents hydroxyl, or
f) $R^1$ represents 4-chlorophenyl,
$R^2$ represents and $R^3$ represents hydroxyl, or
g) Y represents —CH(OH) and
$R^4$ represents chlorine or phenyl, or
h) Y represents CO and
$R^4$ represents chlorine, or
i) $R^5$ represents hydrogen or chlorine the improvement which comprises preventing crystallization of such active compound by including in the solution an alkylcarboxylic acid dimethylamide of the formula (I)

in which R represents alkyl having 5 to 19 carbon atoms, wherein the concentration of said active compound in said aqueous solution is from about 0.0001 to about 3 percent by weight and the weight ratio of said active compound to said alkylcarboxylic acid dimethylamide is from about 1:023 to about 1:5.

* * * * *